United States Patent
Hanna, Jr. et al.

(10) Patent No.: US 6,515,114 B1
(45) Date of Patent: Feb. 4, 2003

(54) BUNTE SALT AZO DYE COMPOUND

(75) Inventors: James Myron Hanna, Jr., Kannapolis, NC (US); Guido Joseph Danhieux, Charlotte, NC (US)

(73) Assignee: Clariant Finance (BVI) Limited, Tortola (VG)

( * ) Notice: Subject to any disclaimer, the term of this patent is extended or adjusted under 35 U.S.C. 154(b) by 0 days.

(21) Appl. No.: 10/166,295

(22) Filed: Jun. 10, 2002

(51) Int. Cl.[7] .......................... C09B 29/30; D06P 1/39; A61K 7/13
(52) U.S. Cl. .................. 534/736; 8/405; 8/428; 8/683
(58) Field of Search ................. 534/736; 8/405, 8/428, 683

(56) References Cited

U.S. PATENT DOCUMENTS

| 2,245,971 A | 6/1941 | Felix et al. ............. 260/205 |
| 3,088,790 A | 5/1963 | Schultheis et al. ............ 8/54.2 |
| 3,226,395 A | 12/1965 | Schmmelschmidt et al. ..... 260/314.5 |
| 3,236,860 A | 2/1966 | Schultheis et al. ....... 260/314.5 |
| 3,334,085 A | 8/1967 | Geselbracht ............... 260/185 |
| 3,415,606 A | 12/1968 | Randebrock ................. 8/10.1 |
| 3,496,207 A | 2/1970 | Barwick et al. ............ 260/453 |
| 3,562,246 A | 2/1971 | Barwick et al. ............ 260/148 |
| 5,964,899 A | 10/1999 | Berenguer et al. ............ 8/436 |
| 6,306,182 B1 | 10/2001 | Chan et al. .................... 8/426 |

FOREIGN PATENT DOCUMENTS

| GB | 953428 | | 3/1964 |
| GB | 1161113 | * | 8/1969 |

OTHER PUBLICATIONS

K. Venkataraman, "The Chemistry of Synthetic Dyes", 1974, vol. 7, Academic Press, Inc., New York, New York, p. 35–68.

H. Distler, "The Chemisy of Bunte Salts", Angew. Chem. Internat. Edit., vol. 6, 1967, No. 6, p. 544–533.

* cited by examiner

Primary Examiner—Fiona T. Powers
(74) Attorney, Agent, or Firm—Richard P. Silverman

(57) ABSTRACT

The invention relates to a Bunte salt azo dye composition comprising an azo dye containing at least one Bunte salt group. The resulting dye is water soluble material which is useful in the rapid dying of natural and synthetic fibers. The Bunte salt azo dye of the present invention can be used without requiring a mordanting step or a concurrent or pre-reducing step to condition fibers of animal hair to accept the dye to achieve strong color performance.

18 Claims, No Drawings

BUNTE SALT AZO DYE COMPOUND

FIELD OF THE INVENTION

The present invention relates to a water soluble azo dye composition containing a Bunte salt group and a method for making the azo dye composition.

BACKGROUND OF THE INVENTION

Bunte salts are generally understood to be alkali-S-alkyl or alkali-S-aryl thiosulfates. As used herein, the concept of a Bunte salt group includes the alkali or ammonium salts of the $-S_2O_3^-$ group which is linked to a carbon atom. Bunte salt dyes are generally disclosed in "The Chemistry of Synthetic Dyes", by Venkataraman, Volume 7, at pages 35 to 68, published in 1968, and hereby incorporated by reference. On page 60, it is specifically stated that when dyeing human hair with a Bunte salt dye, the hair must be first treated with a reducing agent. Bunte salts are hydrolyzed by aqueous acids with the formation of thiols. In alkaline medium they form the corresponding disulfides as well as other products. This reactivity is utilized for fixing dyes with Bunte salt groups on textile materials. The functional groups of the fibers, such as, the OH group of the cellulosics, the amino and thiol groups of wool, or the acid amide groups of synthetic polyamides, act in this reaction as nucleophilic agents. After pretreatment of cellulose with sodium sulfide solution or during the treatment of wool, polycondensation takes place on the substrate with the formation of disulfide bridges. A corresponding dyeing with Bunte salt dyes is therefore washfast. Processes for synthesizing compounds with Bunte salt groups, the properties of these compounds and their use are described in an article by H. Distler, entitled "The Chemistry of Bunte Salts", published in *Angewandte Chemie International Edition*, Volume 6 (1967), No. 6, pages 544–553.

Hair dye compositions use either oxidative dyes or direct dyes. The oxidative dyes lead to shades with better covering power and better staying power, but they have the disadvantage of not being entirely harmless and of requiring an oxidation reaction which is generally accompanied by appreciable degradation of the keratin fibers. In addition, their staying power and their affinity for the hair usually results in the appearance of bands of demarcation between dyed ends and half-lengths and undyed roots.

These problems do not arise in the case of direct dyes. Using of direct dyes has the further advantage over oxidative dye precursors by potentially reducing risks of allergy. Among the direct dyes most commonly used are nitrobenzene derivatives. However, these nitrobenzene dyes do not sufficiently withstand repeated washing. To overcome this flaw, attempts have been made to replace nitrobenzene dyes with aminoanthraquinone dyes or azo dyes.

U.S. Pat. No. 3,334,085 discloses a disazo dyestuff corresponding to the formula:

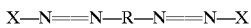

wherein X is a radical of the benzene series bearing a pendant thiosulfate group in a position selected from the group consisting of meta and para with respect to the adjacent azo group, and R is the radical of a naphthol bearing at least one hydroxy substituent in the ortho position to the azo group. The dyestuff is further characterized in that at least one of the radicals of the benzene series positioned ortho to the hydroxy substituent bears in ortho position to the adjoining azo group, a group capable of forming a metal complex of chromium, cobalt, copper, nickel, or iron. The dyestuffs are suitable for coloring fabrics.

U.S. Pat. No. 3,415,606 discloses a method of dyeing human hair which includes treating the hair first in a mordanting step which comprises contacting the hair with a mercaptan which is adapted to form with the keratin of the hair one or more SH groups on the surface of the hair. Subsequently, the treated hair surface is reacted with an azo dye having a Bunte salt group wherein the Bunte salt group is positioned meta to the adjoining azo group and separated from the benzene radical by at least one alkyl group.

U.S. Pat. No. 3,496,207 discloses a method of preparing sulfonaphthylamino thiosulfates for use as dye intermediates for use in making water soluble monoazo dyes for cotton and cellulose fabric.

British Patent No 953,428 discloses water soluble azo-dyestuffs containing one or more thiosulfuric acid groups and processes for their manufacture.

One object of the invention is to provide a novel class of compounds for use in coloring fibers including natural and synthetic fibers such as cotton, nylon, wool, and the like.

Another object of the invention is to provide a class of Bunte salt azo dye compounds for use in coloring animal hair, which can be used in animal hair color systems which are substantially free of reducing or mordanting agents.

SUMMARY OF THE INVENTION

The invention comprises a compound of the formula

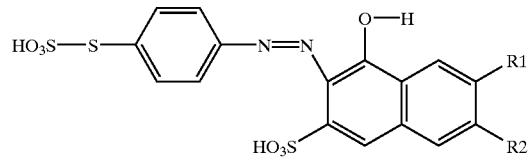

wherein R1 and R2 are either hydrogen or a phenylamino radical such that R1 and R2 are different. The phenylamino radical can comprise phenylamine or a substituted phenylamine having a substituent selected from the group consisting of alkoxy, sulfonate, and thiosulfate. The alkoxy substituent can comprise a methoxy or an ethoxy substituent. The above Bunte salt azo dye composition was discovered to dye animal hair a strong color when applied to animal hair at ambient temperature. Surprisingly, it was discovered that it was not necessary to pre-treat the animal hair with a mordanting or reducing step prior to or simultaneously with the application of the dye. The elimination of the reducing or mordanting step in dyeing animal hair provides significant economic advantages, simplifies the dyeing process, and minimizes damage to the animal hair such as wool and yak hair. The compounds of the present invention were also successfully employed to color fibers such as cotton, nylon and the like.

DETAILED DESCRIPTION OF THE INVENTION

The invention comprises a Bunte salt azo dye compound capable of causing coloration of fibers such as textile fibers and animal fibers such as wool, leather, and animal hair (excluding human hair), and a dye composition containing the Bunte salt azo dye compound. Although Bunte salt dyes have been employed in dyeing fibers, the use of such dyes, particularly for dyeing animal hair has required the pretreatment of the material to be dyed in order for the dye to perform effectively. Examples of combining such reducing or mordanting steps with application of Bunte salt dyes to fibers can be found in U.S. Pat. No. 5,071,641. Unlike the prior art Bunte salt azo type dyes which are generally employed to dye fibers such as animal hair, the Bunte salt group of the present invention is in a para position relative to the azo bond, attached directly to a connecting benzene ring of a phenylamino radical without an intervening carbon or oxygen atom. It is believed that the proximity of the para-Bunte salt group to the azo bond is a critical factor in eliminating the requirement for the mordanting or reducing step. In addition, such conventional Bunte salt azo dyes generally have at least one carbon atom between the Bunte salt group and the benzene ring adjoining the azo bond.

The Bunte salt azo dyes of the present invention are prepared by diazotization of the S-(4-amino phenyl) thiosulfate by reacting the primary aromatic amine with sodium nitrite in the presence of a mineral acid such as hydrochloric acid to form a diazonium salt, followed by a coupling of the diazonium salt under alkaline conditions (at a pH from about 8 to about 10) with a salt of an aryl amino hydroxy naphthalene sulfonic acid, such as phenyl J-acid or phenyl Gamma-acid. Phenyl J-acid is a term of the dye art referring to a compound having the molecular formula $C_{16}H_{13}NO_4S$ such as 2-phenylamino-5-naphthol-7-sulfonic acid, or 6-phenylamino-1-naphtol-3-sulfonic acid. Phenyl Gamma-acid is a term of the dye art referring to a compound having the molecular formula $C_{16}H_{13}NO_4S$ such as 2-phenylaminonaphthalene-8-hydroxy-6-sulfonic acid. The critical aspect of the process of the present invention is to provide a Bunte salt azo dye which includes an azo group having at least one Bunte salt group in a para position on a benzene ring relative to the azo group attached to that benzene ring. The use of the sodium S-(4-amino-phenyl)-thiosulfate as the starting material results in the Bunte salt group being para to the azo bond in the molecule.

THE METHOD OF USE

The invention further comprises a method for coloring keratin fiber such as animal hair including wool and other animal fur comprising directly applying an aqueous based hair dye composition comprising a Bunte salt azo dye compound, without a reducing agent, to animal hair for a period of time sufficient to cause coloration of the animal hair. It was surprisingly discovered that a reducing agent was not required to assist the dye in bonding to the animal hair. The composition is applied to the animal hair and allowed to remain on the hair for about 5 to 50 minutes, depending on the type and texture of the animal hair. The animal hair is then rinsed well with water to remove the composition. The compositions of the present invention are very gentle to the animal hair because they do not require the use of reducing agents to pre-treat the animal hair before the dye is applied. This application method is similar to that described in U.S. Pat. No. 3,415,606 (Example 1), but without the mordanting pretreatment with thioglycolic acid solution. It was noted in U.S. Pat. No. 3,415,606 that hair which had not been subjected to the mordanting pretreatment only dyed very slightly in this manner.

The invention will be further described in connection with the following examples which are set forth for the purposes of illustration only.

EXAMPLES

Example 1

The disodium salt of a red azo dyestuff of the formula

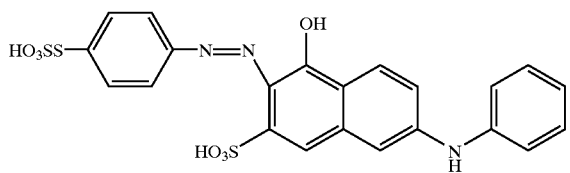

was prepared as follows:

In an 800 ml beaker, 20.5 grams of sodium S-(4-aminophenyl)thiosulfate (prepared as described in U.S. Pat. No. 3,562,246) was diazotized in the conventional manner by adding sodium S-(4-aminophenyl)thiosulfate to 325 ml of 2.8% hydrochloric acid, cooling the mixture to <5° C. by the direct addition of ice, then adding 18.1 grams of a 40% aqueous solution of sodium nitrite. The resulting diazo slurry was then added to the solution made in a 2000 ml beaker from 400 ml of water, 37.7 grams of phenyl J-acid, and 9.2 grams of sodium carbonate. The addition of the diazo slurry was made while maintaining the temperature at about 7° C. by the direct addition of ice, and maintaining the pH of the composition at about 8 by the addition of 20% aqueous sodium carbonate. The composition was then stirred 16 hrs, while allowing the temperature to rise to about 20° C. The dye was salted out with about 90 grams of sodium chloride, filtered, washed with about 1000 ml of 20% aqueous sodium chloride, dried, and ground, yielding about 34 g of dye powder.

Example 2

The disodium salt of a brown azo dyestuff of the formula

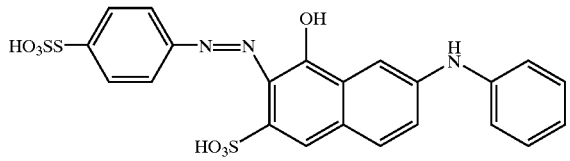

was prepared as described in Example 1, except that 37.7 grams of phenyl Gamma-acid was substituted for the phenyl J-acid.

Example 3

The dye prepared in Example 1 was applied to virgin yak hair in the manner described below:

A bundle of virgin yak hair (weighing about 3 grams) was immersed in a 150 ml beaker containing 75 ml of a 3% slurry of the dye in water, which had been adjusted to pH 9 with aqueous ammonia. The immersion was carried out for 30 minutes at ambient temperature. The yak hair bundle was removed and rinsed thoroughly with ambient temperature water, then dried. The yak hair was dyed a strong red color (CIELab dE =50.11 vs. the originally undyed yak hair). The CIELab dE is the total color difference between the dyed sample and a standard, in this case the undyed hair or fiber, as measured by a Datacolor Spectraflash 600 reflectance spectrophotometer. The CIELab dE reading provides a measure of the dye uptake on the fibers.

Example 4

The dyed yak hair prepared in Example 3 was washed at 25° C. with a 1% solution of a generic shampoo containing ammonium lauryl sulfate and ammonium laureth sulfate (Suave, a Trademark of Helene Curtis, Naturals Fresh Mountain Strawberry), then rinsed thoroughly with water at a temperature of 25° C. This was repeated 5 times. A minor amount of color loss was seen (Reflectance strength=86% compared to the dyed hair of Example 3).

Example 5

The dye prepared in Example 1 was applied to cotton in the manner described below:

A swatch of mercerized cotton fabric (weighing about 3 grams) was immersed in a 400 ml beaker containing 200 ml of a 3% slurry of the dye in water and about 0.05 g of Sandopan DTC-100. This mixture was heated to 90° C. for 5 minutes, after which time the mixture was cooled to 50° C. The fabric was removed and rinsed thoroughly with water at ambient temperature. The cotton had been dyed a strong red color (CIELab dE=75.8 vs. the originally undyed cotton fabric).

Example 6

The dye prepared in Example 1 was applied to nylon in the manner described below.

A swatch of nylon fabric (weighing about 3 grams) was immersed in a 400 ml beaker containing 200 ml of a 3% slurry of the dye in water, 2.0 g of acetic acid, and 4.0 g of sodium acetate. This mixture was heated to the boil for 10 minutes, after which time the mixture was cooled to 50° C. The fabric was removed and rinsed thoroughly with water at ambient temperature. The nylon had been dyed a strong red color (CIELab dE=83.8 vs. the undyed nylon fabric).

Example 7

The dye prepared in Example 1 was applied to wool, in the manner described below.

A swatch of wool fabric (weighing about 3 grams) was immersed in a 400 ml beaker containing 200 ml of a 0.03% solution of the dye in water, 6.0 g of sulfuric acid, and 20.0 g of sodium sulfate. This mixture was heated to the boil for 10 minutes, after which time the mixture was cooled to 50° C. The fabric was removed and rinsed thoroughly with water at ambient temperature. The wool had been dyed a strong red color (CIELab dE=73.6 vs. the undyed wool fabric).

We claim:

1. A dye compound of the formula (1)

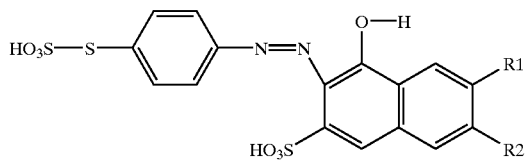

wherein R1 and R2 are either hydrogen or a phenylamino radical, and R1 and R2 are different.

2. The dye compound of claim 1 wherein the phenylamino radical is a phenylamine or a substituted phenylamine, wherein the substituted phenylamine has a substituent selected from the group consisting of alkoxy, sulfonate, and thiosulfate substituents.

3. The dye compound of claim 2 wherein the alkoxy substituent is a methoxy or an ethoxy substituent.

4. A red dye comprising the dye compound of claim 1 wherein R1 is hydrogen and R2 is a phenylamino radical.

5. A brown dye comprising the dye compound of claim 1 wherein R2 is hydrogen and R1 is a phenylamino radical.

6. A process for dyeing a fiber consisting essentially of directly contacting the fiber with a dye formulation comprising the dye compound of claim 1.

7. The process of claim 6 wherein the fiber is an unmordanted fiber of cotton or nylon.

8. The process of claim 6 wherein the fiber comprises an unmordanted fiber of animal hair, excluding human hair.

9. The process of claim 6 wherein the fiber comprises wool.

10. The process of claim 6 wherein said process comprises a contacting time of about 5 to about 50 minutes at a temperature at or above ambient temperature.

11. The process of claim 6 wherein said direct contacting comprises a pH from about 3 to about 10.

12. The process of claim 6 wherein said direct contacting comprises a pH in an alkaline range.

13. The process of claim 12 wherein said alkaline range comprises a pH from about 8 to about 10.

14. A process for producing a Bunte salt azo dye comprising:
    a) diazotizing S-(4-aminophenyl) thiosulfate a to provide a diazonium salt;
    b) coupling the diazonium salt under alkaline conditions to a salt of an aryl-amino-hydroxy-naphthalene sulfonic acid to provide the Bunte salt azo dye.

15. The process of claim 14 wherein the salt of aryl amino hydroxy naphthalene sulfonic acid comprises phenyl-J acid or phenyl-Gamma acid.

16. A process for producing a red Bunte salt azo dye comprising:
    a) diazotizing S-(4-aminophenyl) thiosulfate to provide a diazonium salt;
    b) coupling the diazonium salt under alkaline conditions with 2-phenylamino-5-naphthol-7-sulfonic acid, or 6-phenylamino-1-naphthol-3-sulfonic acid to provide the red Bunte salt azo dye.

17. A process for producing a brown Bunte salt azo dye comprising:
    a) diazotizing S-(4-aminophenyl) thiosulfate to provide a diazonium salt;
    b) coupling the diazonium salt under alkaline conditions to 2-phenylamino-naphthalene-8-hydroxy-6-sulfonic acid to provide the brown Bunte salt azo dye.

18. The process of claim 14 wherein the Bunte salt azo dye includes an azo group having at least one Bunte salt group in a para position on a benzene ring relative to the azo group attached to the benzene ring.

* * * * *